United States Patent [19]
Krause

[11] Patent Number: 6,117,909
[45] Date of Patent: Sep. 12, 2000

[54] METHODS OF USING SULFAMIC ACID DERIVATIVES FOR LOWERING SERUM OR PLASMA LEVEL OF LP(A)

[75] Inventor: Brian Robert Krause, Ann Arbor, Mich.

[73] Assignee: Warner-Lambert Company, Morris Plains, N.J.

[21] Appl. No.: 09/000,296

[22] PCT Filed: Jul. 8, 1996

[86] PCT No.: PCT/US96/11366

§ 371 Date: Jan. 26, 1998

§ 102(e) Date: Jan. 26, 1998

[87] PCT Pub. No.: WO97/05868

PCT Pub. Date: Feb. 20, 1997

Related U.S. Application Data

[60] Provisional application No. 60/003,031, Aug. 3, 1995.

[51] Int. Cl.⁷ .................................................. A61K 31/18
[52] U.S. Cl. ........................... 514/602; 514/605; 514/824
[58] Field of Search .................... 514/602, 605, 514/824

[56] References Cited

U.S. PATENT DOCUMENTS

| | | | |
|---|---|---|---|
| 5,003,106 | 3/1991 | De Vries | 564/54 |
| 5,245,068 | 9/1993 | Picard et al. | 558/49 |
| 5,491,172 | 2/1996 | Lee et al. | 514/602 |

FOREIGN PATENT DOCUMENTS

| | | |
|---|---|---|
| 0512570 | 11/1992 | European Pat. Off. |
| 9207826 | 5/1992 | WIPO |
| 9426702 | 11/1994 | WIPO |

OTHER PUBLICATIONS

PCT International Search Report, PCT/US96/11366.

*Primary Examiner*—Kimberly Jordan
*Attorney, Agent, or Firm*—Elizabeth M. Anderson

[57] ABSTRACT

The present invention is directed to new therapeutic uses of compounds of formula:

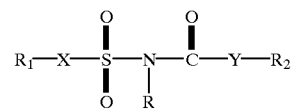

wherein X and Y are oxygen, sulfur, or $(CR'R'')_n$ wherein n is 1 to 4; R is hydrogen, alkyl, or benzyl; $R_1$ and $R_2$ are phenyl, substituted phenyl, naphthyl, substituted naphthyl, an aralkyl group, an alkyl chain, adamantyl, or a cycloalkyl group. The uses are cerebrovascular disease such as stroke, peripheral vascular diseases, and restenosis.

23 Claims, No Drawings

METHODS OF USING SULFAMIC ACID DERIVATIVES FOR LOWERING SERUM OR PLASMA LEVEL OF LP(A)

This application is a 371 of PCT/US96/11366 filed Jul. 8, 1996, which claims benefit of Provisional Appl. No. 60/003,031 filed Aug. 3, 1995.

BACKGROUND OF INVENTION

The compounds of the instant invention are fully described in copending U.S. application Ser. No. 08/223,932 filed Apr. 13, 1994 now U.S. Pat. No. 5,491,172. The use of the compounds taught is hypercholesterolemia and atherosclerosis. This application is hereby incorporated by reference.

The compounds of the copending application show increased chemical stability over those of U.S. Pat. No. 5,245,068.

The present invention relates generally to lipoprotein(a), Lp(a), and more particularly to methods and agents to lower its plasma concentrations to achieve therapeutic benefit.

The macromolecule known as lipoprotein(a), or Lp(a), is a complex of low-density lipoproteins (LDL), and a hydrophilic glycoprotein that has been given the name apolipoprotein(a), or apo(a). The principal protein of LDL is apo B-100, and apo(a) is attached to the apo B moiety of LDL by a disulfide bond. LDL is the major transporter of cholesterol in human plasma. The physiological function of Lp(a) is unknown.

Apo(a) is not similar in structure to other apolipoproteins but exhibits similarity to another plasma protein called plasminogen. The structure of plasminogen includes five tandemly repeated homologous domains called kringles (Kringles I–V), which are pretzel-like structures stabilized by three internal disulfide bridges followed by a protease domain. Kringle structures have been identified in various other proteins such as prothrombin, tissue-type plasminogen activator (t-PA), urokinase and coagulation Factor XII (Utermann, *Science,* 1989;246:904–910). Apo(a) lacks kringles similar to I to III of plasminogen but has multiple copies of the kringle domain similar to the fourth one of plasminogen, and a single copy of a kringle domain similar to the fifth one of plasminogen (kringle-5). Apo(a) also contains a protease domain.

Lp(a) was first identified by Berg in 1963 (Berg, *Acta Pathol. Microbiol. Scand.,* 1963;59:369) as an antigenic activity associated with the LDL fraction in the plasma of some individuals. Plasma Lp(a) levels vary in different individuals from less than 2 mg/dL to greater than 200 mg/dL. Increased plasma Lp(a) levels are considered to be a risk factor for atherosclerosis, either alone or in conjunction with elevated LDL levels (Kostner, et al., *Circulation,* 1989;80(5):1313–1319 citing previous investigators) The plasma concentration of Lp(a) and the size of apo(a) are genetically determined (Gavish, et al., *J. Clin. Invest.,* 1989;84:2021–2027).

The discovery of the homology of apo(a) to plasminogen has prompted further investigation as to the role played by Lp(a). Hajjar, et al., *Nature,* 1989;339:303–305 considered the similarity between the apo(a) component of Lp(a) and plasminogen and investigated the effect that Lp(a) might have on the interaction between plasminogen and the endothelial cell, and found that Lp(a) competed for plasminogen binding sites and appeared to be capable of inhibiting the activation of plasminogen on the surface of endothelial cells by t-PA. This suggests that elevated levels of Lp(a) might impair and inhibit cell surface fibrinolysis, thus interfering with the fibrinolytic system. In Kostner, et al. (vide supra), HMG-COA reductase inhibitors such as simvastatin and lovastatin, as well as other known cholesterol-lowering agents were administered to a test group of patients, and plasma samples thereafter were taken and examined. Most of the tested agents failed to lower Lp(a) levels, and, in fact, in some instances, Lp(a) levels appeared to rise, possibly due to stimulation of Lp(a) production. The authors identified only two agents, namely neomycin and niacin, that decreased both LDL and Lp(a) levels. These agents only lower Lp(a) to a limited extent and because of this, as well as toxic side effects, do not appear to present a viable therapeutic avenue.

A need, therefore, exists for an effective method and associated agents for decreasing plasma Lp(a) levels.

The role of lipoprotein(a) has been studied in patients suffering from ischemic cerebrovascular disease and it has been determined they have significantly higher levels of lipoprotein(a), lipids carried by intermediate-density proteins, low-density lipoprotein cholesterol, and lower levels of high-density lipoproteins than control subjects. These then are major risk factors for ischemic cerebrovascular disease (Pedro-Botck, *Stroke,* 1992;23(11):1556–1562).

Lipoprotein(a) is a genetic, independent, and critical risk factor for ischemic stroke, especially in young adults (Nagayama, *Stroke,* 1994;25(1):74–78).

High serum lipoprotein(a) levels are an independent risk factor in the development of cerebral infarction (Shintani, *Stroke,* 1993;24(7):965–969.

Elevated plasma levels of Lp(a) lipoprotein have been linked to the development of premature atherosclerosis in coronary circulation (Valentine, *Arch. Intern. Med.,* 1994;154:801–806).

The prevention of restenosis after percutaneous transluminal coronary angioplasty by reducing lipoprotein(a) levels with low-density lipoprotein apheresis is reported in Daida, *Am. J. Card.,* 1994;73(15):1037–1040.

Serum Lp(a) is an independent factor associated with stenosis of saphenous vein grafts (Hoff, *Circulation,* 1988;77(6):1238–1243.

SUMMARY OF THE INVENTION

The present invention is directed to new uses of compounds of Formula I below.

The compounds are those of formula:

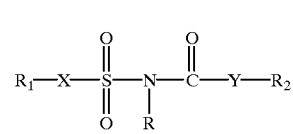

or a pharmaceutically acceptable salt thereof wherein:

X and Y are selected from oxygen, sulfur and $(CR'R'')_n$, wherein n is an integer of from 1 to 4 and R' and R'' are each independently hydrogen, alkyl, alkoxy, halogen, hydroxy, acyloxy, cycloalkyl, phenyl optionally substituted or R' and R'' together form a spirocycloalkyl or a carbonyl; with the proviso at least one of X and Y is $-(CR'R'')_n-$ and with the further proviso when X and Y are both $(CR'R'')_n$ and R' and R'' are hydrogen and n is one, $R_1$ and $R_2$ are aryl;

R is hydrogen, a straight or branched alkyl of from 1 to 8 carbon atoms or benzyl;

$R_1$ and $R_2$ are each independently selected from (a) phenyl or phenoxy each of which is unsubstituted or is substituted with 1 to 5 substituents selected from
   phenyl,
   an alkyl group having from 1 to 6 carbon atoms and which is straight or branched,
   an alkoxy group having from 1 to 6 carbon atoms and which is straight or branched;
   phenoxy,
   hydroxy,
   fluorine,
   chlorine,
   bromine,
   nitro,
   trifluoromethyl,
   —COOH,
   —COOalkyl wherein alkyl has from 1 to 4 carbon atoms and is straight or branched,
   —$(CH_2)_p NR_3 R_4$ wherein p is zero or one, and each of $R_3$ and $R_4$ is selected from hydrogen or a straight or branched alkyl group having 1 to 4 carbon atoms;

(b) 1- or 2-naphthyl unsubstituted or substituted with from 1 to 3 substituents selected from
   phenyl,
   an alkyl group having from 1 to 6 carbon atoms and which is straight or branched,
   an alkoxy group having from 1 to 6 carbon atoms and which is straight or branched;
   hydroxy,
   phenoxy,
   fluorine,
   chlorine,
   bromine,
   nitro,
   trifluoromethyl,
   —COOH,
   —COOalkyl wherein alkyl has from 1 to 4 carbon atoms and is straight or branched,
   —$(CH_2)_p NR_3 R_4$ wherein p, $R_3$ and $R_4$ have the meanings defined above;

(c) arylalkyl;

(d) a straight or branched alkyl chain having from 1 to 20 carbon atoms and which is saturated or contains from 1 to 3 double bonds; or (e) adamantyl or a cycloalkyl group wherein the cycloalkyl moiety has from 3 to 6 carbon atoms; with the provisos:

(i) where X is $(CH_2)_n$, Y is oxygen, and $R_1$ is a substituted phenyl, then $R_2$ is a substituted phenyl;

(ii) where Y is oxygen, X is $(CH_2)_n$, $R_2$ is phenyl or naphthyl, then $R_1$ is not a straight or branched alkyl chain; and (iii) the following compounds are excluded:

| X | Y | R | $R_1$ | $R_2$ |
|---|---|---|---|---|
| $CH_2$ | O | H | $(CH_2)_2 CH_3$ | Ph |
| $CH_2$ | O | H | $CH_3$ | Ph |
| $CH_2$ | O | H | | i-Pr. |

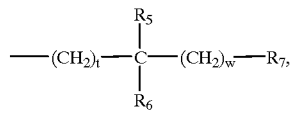

Preferred compounds of the instant invention are those of Formula I:

wherein $R_1$ is phenyl or is phenyl disubstituted in the 2,6-positions, wherein $R_2$ is phenyl or is phenyl disubstituted in the 2,6-positions, wherein each of $R_1$ and $R_2$ is phenyl, wherein each phenyl is disubstituted in the 2,6-position, wherein $R_1$ is phenyl disubstituted in the 2,6-positions and $R_2$ is phenyl trisubstituted in the 2,4,6-positions, wherein $R_1$ is 2,6-bis(1-methylethyl)phenyl and $R_2$ is 2,6-bis(1-methylethyl)phenyl or 2,4,6-tris(1-methyl-ethyl)phenyl, wherein one of $R_1$ and $R_2$ is the group $$—(CH_2)_t—\underset{R_6}{\overset{R_5}{C}}—(CH_2)_w—R_7,$$

wherein t is zero or 1 to 4; w is zero or 1 to 4 with the proviso that the sum of t and w is not greater than 5; $R_5$ and $R_6$ are each independently selected from hydrogen or alkyl having from 1 to 6 carbon atoms, or when $R_5$ is hydrogen, $R_6$ can be selected from the groups defined for $R_7$; and $R_7$ is phenyl or phenyl substituted with from 1 to 3 substituents selected from a straight or branched alkyl group having from 1 to 6 carbon atoms, straight or branched alkoxy group having from 1 to 6 carbon atoms, phenoxy, hydroxy, fluorine, chlorine, bromine, nitro, trifluoromethyl, —COOH, Cooalkyl wherein alkyl has from 1 to 4 carbon atoms, or —$(CH_2)_p NR_3 R_4$ wherein P, $R_3$ and $R_4$ have the meanings defined above.

Also preferred compounds of the instant invention are those of Formula I wherein X is oxygen, sulfur or $(CR'R'')_n$;

Y is oxygen, sulfur or $(CR'R'')_n$, with the proviso that at least one of X or Y is $(CR'R'')_n$ wherein n is an integer of from 1 to 4 and R' and R'' are each independently hydrogen, straight or branched alkyl of from 1 to 6 carbons, optionally substituted phenyl, halogen, hydroxy, alkoxy, acyloxy, cycloalkyl, or R' and R'' taken together form a carbonyl or a spirocycloalkyl group of from 3 to 10 carbons;

R is hydrogen;

$R_1$ is phenyl optionally substituted, straight or branched alkyl of from 1 to 10 carbon atoms, cycloalkyl of from 3 to 10 carbon atoms;

$R_2$ is phenyl optionally substituted, straight or branched alkyl of from 1 to 10 carbon atoms, cycloalkyl of from 3 to 8 carbon atoms, phenoxy optionally substituted with the proviso that only if X is $(CR'R'')_n$ can $R_1$ be optionally substituted phenoxy and only if Y is $(CR'R'')_n$ can $R_2$ be optionally substituted phenoxy, and with the further proviso that at least one of $R_1$ and $R_2$ is optionally substituted phenyl or phenoxy.

More preferred compounds of the instant invention are those of Formula I wherein X is oxygen;

Y is $(CR'R'')_n$ wherein n is an integer of from 1 to 2;

R is hydrogen;

$R_1$ is optionally substituted phenyl;

$R_2$ is optionally substituted phenyl or phenoxy, straight or branched alkyl of from 1 to 10 carbons, or cycloalkyl of from 3 to 10 carbons; and R' and R'' are each independently hydrogen, straight or branched alkyl of from 1 to 6 carbons, optionally substituted phenyl, halogen, hydroxy, alkoxy, acyloxy, cycloalkyl, or R' and R" taken together form a carbonyl or a spirocycloalkyl.

DETAILED DESCRIPTION OF THE INVENTION

The compounds useful in the present invention provide a class of N-acyl sulfamic acid esters (or thioesters), N-acyl sulfonamides, and N-sulfonyl carbamic acid esters (or thioesters) which are ACAT inhibitors, now found to be useful in treating cerebrovascular disease such as stroke, peripheral vascular disease, and restenosis. The compounds of the present invention have been found to be effective in lowering Lp(a).

In Formula I above, illustrative examples of straight or branched saturated hydrocarbon chains having from 1 to 20 carbon atoms include methyl, ethyl, n-propyl, isopropyl, n-butyl, iso-butyl, tert-butyl, n-pentyl, isopentyl, n-hexyl, a-heptyl, n-octyl, n-undecyl, n-dodecyl, n-hexadecyl, 2,2-dimethyldodecyl, 2-tetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

Illustrative examples of straight or branched alkyl groups having from 1 to 6 carbon atoms as used in Formula I include methyl, ethyl, n-propyl, isopropyl, n-pentyl, n-butyl, and tert-butyl.

Illustrative examples of cycloalkyl groups, as used in Formula I, include cyclopentyl, cyclohexyl, cyclooctyl, tetrahydronaphthyl, and 1- or 2-adamantyl.

Spirocycloalkyl groups are, for example, spirocyclopropyl, spirocyclobutyl, spirocyclopentyl, and spirocyclohexyl.

Illustrative examples of arylalkyl groups are: benzyl, phenethyl, 3-phenylpropyl, 2-phenylpropyl, 4-phenylbutyl, 2-phenylbutyl, 3-phenylbutyl, benzhydryl, 2,2-diphenylethyl, and 3,3-diphenylpropyl.

Pharmaceutically acceptable salts of the compounds of Formula I are also included as a part of the present invention.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Berge SN, et al, *J. Pharm. Sci.,* 1977;66:1–19.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

The compounds of the present invention may also exist in different stereoisomeric forms by virtue of the presence of asymmetric centers in the compound. The present invention contemplates all stereoisomeric forms of the compounds as well as mixtures thereof, including racemic mixtures.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

Preferred compounds of the present invention are those wherein one of $R_1$ and $R_2$ is phenyl, and more preferably wherein one of $R_1$ and $R_2$ is substituted phenyl, and still more preferably wherein one of $R_1$ and $R_2$ is phenyl disubstituted in the 2,6-positions.

In one preferred embodiment both $R_1$ and $R_2$ are phenyl disubstituted in the 2,6-positions. In another preferred embodiment $R_1$ is phenyl disubstituted in the 2,6-position and $R_2$ is trisubstituted in the 2,4,6-positions.

In another preferred embodiment of the present invention, $R_1$ is 2,6-bis(1-methylethyl)phenyl; and $R_2$ is 2,6-bis(1-methylethyl)phenyl or 2,4,6-tris(1-methylethyl)phenyl.

Preferred compounds of Formula I include, but are not limited to the following:

Sulfamic acid (phenylacetyl)-2,6-bis(1-methylethyl)phenyl ester,

Sulfamic acid[[2,4,6-tris(1-methylethyl)phenyl]-acetyl-2,6-bis(1-methylethyl)phenyl ester, Sulfamic acid[[2,6-bis(1-methylethyl)phenyl]-acetyl]-2,6-bis(1-methylethyl)phenyl ester, Sulfamic acid [[2,4,6-tris(1-methylethyl)phenyl]-acetyl-2,4,6-tris(1-methylethyl)phenyl ester, Sulfamic acid[[2,6-bis(1-methylethyl)phenyl]-acetyl]-2,4,6-tris(1-methylethyl)phenyl ester, Sulfamic acid[adamantaneacetyl]-2,6-bis[1-methylethyl)phenyl ester, Sulfamic acid[[2,6-bis(1-methylethyl)phenyl]-acetyl]-2,6-bis(1-methylethyl)phenyl ester-sodium salt, Sulfamic acid[[2,4,6-tris(1-methylethyl)phenyl]-acetyl]-2,6-bis(1-methylethyl)phenyl ester-sodium salt, Sulfamic acid (decanoyl)-2,6-bis-(1-methylethyl)-phenyl ester, Sulfamic acid (dodecanoyl)-2,6-bis-(1-methylethyl) phenyl ester, 2,6-Bis(1-methylethyl)-N-[[[2,4,6-tris(1-methylethyl)phenyl]methyl]sulfonyl]benzeneacetamide, 2,6-Bis(1-methylethyl)-N-[[[2,4,6-tris-(1-methylethyl)phenyl]methyl]sulfonyl]benzeneacetamide-sodium salt, 2,6-Bis(1-methylethyl)phenyl[[[2,4,6-tris-(1-methylethyl)phenyl]methyl]sulfonyl]carbamate, 2,6-Bis(1-methylethyl)phenyl[[[2,4,6-tris-(1-methylethyl)phenyl]methyl]sulfonyl]carbamate-sodium salt, Sulfamic acid (1-oxo-3,3-diphenylpropyl)-2,6-bis(1-methylethyl)phenyl ester, Sulfamic acid [2,6-dichlorophenyl(acetyl)]-2,6-bis(1-methylethyl)phenyl ester, Sulfamic acid [2,6-dichlorophenyl(acetyl)]-2,6-bis(1-methylethyl)phenyl ester, Sulfamic acid trans-[(2-phenylcyclopropyl)-carbonyl]-2,6-bis(1-methylethyl)phenyl ester, Sulfamic acid [2,5-dimethoxyphenyl(acetyl)]-2,6-bis(1-methylethyl)phenyl ester, Sulfamic acid [2,4,6-trimethoxyphenyl(acetyl)]-2,6-bis(1-methylethyl)phenyl ester, Sulfamic acid [2,4,6-trimethylphenyl(acetyl)]-2,6-bis(1-methylethyl)phenyl ester, Sulfamic acid [2-thiophenyl(acetyl)]-2,6-bis(1-methylethyl)phenyl ester, Sulfamic acid [3-thiophenyl(acetyl)]-2,6-bis(1-methylethyl)phenyl ester, Sulfamic acid [2-methoxyphenyl(acetyl)]-2,6-bis(1-methylethyl)phenyl ester, Sulfamic acid (oxophenylacetyl)-2,6-bis(1-methylethyl)phenyl ester, Sulfamic acid [2-trifluoromethylphenyl(acetyl)]-2,6-bis(1-methylethyl)phenyl ester, Sulfamic acid (1-oxo-2-phenylpropyl)-2,6-bis(1-methylethyl)phenyl ester, Sulfamic acid (cyclopentylphenylacetyl)-2,6-bis(1-methylethyl)phenyl ester, Sulfamic acid (cyclohexylacetyl)-2,6-bis(1-methylethyl)phenyl ester, Sulfamic acid (diphenylacetyl)-2,6-bis(1-methylethyl)phenyl ester, Sulfamic acid (triphenylacetyl)-2,6-bis(1-methylethyl)phenyl ester, Sulfamic acid [(1-phenylcyclopentyl)carbonyl]-2,6-bis(1-methylethyl)phenyl ester, Sulfamic acid (3-methyl-1-oxo-2-phenylpentyl)-2,6-bis(1-methylethyl)phenyl ester, Sulfamic acid (1-oxo-2-phenylbutyl)-2,6-bis(1-methylethyl)phenyl ester, Sulfamic acid (cyclohexylphenylacetyl)-2,6-bis(1-methylethyl)phenyl ester, Sulfamic acid (1-oxo-2,2-diphenylpropyl)-2,6-bis(1-methylethyl)phenyl ester, Sulfamic acid [(9H-fluoren-9-yl)carbonyl]-2,6-bis(1-methylethyl)phenyl ester, Sulfamic acid (1-oxo-3-phenylpropyl)-2,6-bis(1-methylethyl)phenyl ester, Sulfamic acid [1-oxo-3-[2,4,6-tris(1-methylethyl)-phenyl]-2-propenyl]-2,6-bis(1-methylethyl)phenyl ester, Sulfamic acid [1-oxo-3-[2,4,6-tris(1-methylethyl)-phenyl]propyl]-2,6-bis(1-methylethyl)phenyl ester, Sulfamic acid [(acetyloxy)[2,4,6-tris(1-methyl-ethyl)phenyl]acetyl]-2,6-bis(1-methylethyl)phenyl ester, Sulfamic acid [hydroxy[2,4,6-tris(1-methylethyl)-phenyl]acetyl]-2,6-bis(1-methylethyl)phenyl ester, Sulfamic acid [fluoro[2,4,6-tris(1-methylethyl)-phenyl]acetyl]-2,6-bis(1-methylethyl)phenyl ester, Sulfamic acid (3-methyl-1-oxo-2-phenylpentyl)-2,6-bis(1-methylethyl)phenyl ester sodium salt, Sulfamic acid [[2,4,6-tris(1-methylethyl)phenoxy]-acetyl]-2,6-bis(1-methylethyl)phenyl esters, Sulfamic acid [[2,6-bis(1-methylethyl)phenoxy]-acetyl]-2,6-bis(1-methylethyl)phenyl ester, and Sulfamic acid [[2,4,6-tris(1-methylethyl)phenyl]-acetyl]-2,6-bis(phenyl)phenyl ester.

The ability of the compounds of the present invention to lower Lp(a) is summarized in Table I below. The procedure was: nine male cynomolgus monkeys (*Macaca fascicularis*, 4–5 kg) were maintained on a standard monkey chow diet (containing less than 5% fat and only trace amounts of cholesterol). The diet was available daily from 9 AM until 2 PM. These animals transport approximately equal amounts of cholesterol in HDL (47%) and LDL (51%) and have low triglycerides compared to humans (approximately 50 mg/dL). Five weekly blood samples were taken from anesthetized, restrained animals, and then the animals were dosed with sulfamic acid [[2,4,6-tris-(1-methyl-ethyl)phenyl]acetyl-2,6-bis(1-methylethyl)phenyl ester (hereinafter the compound) daily before meals (for 3 weeks at 30 mg/kg) by incorporating it into oatmeal cream pies (Little Debbie Snack Cakes, McKee Foods, Collegedale, Tenn.). Tang breakfast beverage crystals (Kraft General Foods, Inc., White Plains, N.Y.), and additional cream filling was also added to individual servings. Most animals consumed the drug-containing treat immediately since they were without food during the night. They were not given their daily meal until they consumed the treat. Mean plasma cholesterol (top line) and Lp(a) (bottom line) values are shown below (all values in mg/dL). The drug treatment was in Weeks 6 to 8 and are bolded in Table I.

TABLE I

| Week | | | | | | | | | | | |
|---|---|---|---|---|---|---|---|---|---|---|---|
| 1 | 2 | 3 | 4 | 5 | 6 | 7 | 8 | 9 | 10 | 11 | 12 |
| 147 | 147 | 155 | 155 | 167 | 112 | 112 | 111 | 117 | 128 | 127 | 160 |
| 17.1 | 18.9 | 15.1 | 13.8 | 18.2 | 13.6 | 12.5 | 11.4 | 13.6 | 17.7 | 18.7 | 21.3 |

The average baseline values for cholesterol and Lp(a) were 154 and 16.6 mg/dL, respectively. Using these values, the percentage decreases for cholesterol and Lp(a) are 28% and 31%, respectively. It is important to note that every animal demonstrated a decrease in cholesterol and Lp(a), i.e., there were no nonresponders to the compound. The decrease in total cholesterol was due primarily to a decrease in LDL-cholesterol.

The compounds of the present invention are thus useful in pharmaceutical formulations for the treatment of stroke, peripheral vascular disease, and restenosis.

In therapeutic use as agents for treating stroke, peripheral vascular disease, and restenosis, the compounds of Formulas I or II or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

What is claimed is:

1. A method for lowering the serum or plasma level of Lp(a) in a mammal in need thereof, comprising administering to said mammal an amount effective for lowering the serum or plasma level of said Lp(a) of a compound of formula:

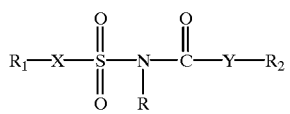

I or a pharmaceutically acceptable salt thereof wherein:

X and Y are selected from oxygen, sulfur and $(CR'R'')_n$ wherein n is an integer of from 1 to 4 and R' and R'' are each independently hydrogen, alkyl, alkoxy, halogen, hydroxy, acyloxy, cycloalkyl, phenyl optionally substituted or R' and R'' together form a spirocycloalkyl or a carbonyl; with the proviso at least one of X and Y is $(CR'R'')_n$ and with the further proviso when X and Y are both $(CR'R'')_n$ and R' and R'' are hydrogen and n is one, $R_1$ and $R_2$ are aryl;

R is hydrogen, a straight or branched alkyl of from 1 to 8 carbon atoms or benzyl;

$R_1$ and $R_2$ are each independently selected from (a) phenyl or phenoxy each of which is unsubstituted or is substituted with 1 to 5 substituents selected from phenyl,
an alkyl group having from 1 to 6 carbon atoms and which is straight or branched,
an alkoxy group having from 1 to 6 carbon atoms and which is straight or branched;
phenoxy,
hydroxy,
fluorine,
chlorine,
bromine,
nitro,
trifluoromethyl,
—COOH,
—COOalkyl wherein alkyl has from 1 to 4 carbon atoms and is straight or branched,
—$(CH_2)_p NR_3 R_4$ wherein p is zero or one, and each of $R_3$ and $R_4$ is selected from hydrogen or a straight or branched alkyl group having 1 to 4 carbon atoms;

(b) 1- or 2-naphthyl unsubstituted or substituted with from 1 to 3 substituents selected from
phenyl,
an alkyl group having from 1 to 6 carbon atoms and which is straight or branched,
an alkoxy group having from 1 to 6 carbon atoms and which is straight or branched;
hydroxy,
phenoxy,
fluorine,
chlorine,
bromine,
nitro,
trifluoromethyl,
—COOH, —COOalkyl wherein alkyl has from 1 to 4 carbon atoms and is straight or branched,
—$(CH_2)_p NR_3 R_4$ wherein p, $R_3$ and $R_4$ have the meanings defined above;

(c) arylalkyl;

(d) a straight or branched alkyl chain having from 1 to 20 carbon atoms and which is saturated or contains from 1 to 3 double bonds; or (e) adamantyl or a cycloalkyl group wherein the cycloalkyl moiety has from 3 to 6 carbon atoms;

with the provisos:

(i) where X is $(CH_2)_n$, Y is oxygen, and $R_1$ is a substituted phenyl, then $R_2$ is a substituted phenyl;

(ii) where Y is oxygen, X is $(CH_2)_n$, $R_2$ is phenyl or naphthyl; then $R_1$ is not a straight or branched alkyl chain; and (iii) the following compounds are excluded:

| X | Y | R | $R_1$ | $R_2$ |
|---|---|---|---|---|
| $CH_2$ | O | H | $(CH_2)_2 CH_3$ | Ph |
| $CH_2$ | O | H | $CH_3$ | Ph |
| $CH_2$ | O | H | 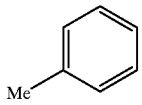 | i-Pr. |

2. A method according to claim 1 wherein $R_1$ is phenyl.

3. A method according to claim 2 wherein $R_1$ is phenyl disubstituted in the 2,6-positions.

4. A method according to claim 1 wherein $R_2$ is phenyl.

5. A method according to claim 4 wherein $R_2$ is phenyl disubstituted in the 2,6-positions.

6. A method according to claim 1 wherein each of $R_1$ and $R_2$ is phenyl.

7. A method according to claim 6 wherein each phenyl is disubstituted in the 2,6-positions.

8. A method according to claim 1 wherein $R_1$ is phenyl disubstituted in the 2,6-positions and $R_2$ is phenyl trisubstituted in the 2,4,6-positions.

9. A method according to claim 1 wherein $R_1$ is 2,6-bis(1-methylethyl)phenyl and $R_2$ is 2,6-bis(1-methylethyl)phenyl or 2,4,6-tris-(1-methylethyl)phenyl.

10. A method according to claim 1 wherein $R_1$ is phenyl or phenyl disubstituted in the 2,6-positions, wherein $R_2$ is phenyl or is phenyl disubstituted in the 2,6-positions, wherein each of $R_1$ and $R_2$ is phenyl, wherein each phenyl is disubstituted in the 2,6-position, wherein $R_1$ is phenyl disubstituted in the 2,6-positions and $R_2$ is phenyl trisubstituted in the 2,4,6-positions, wherein $R_1$ is 2,6-bis(1-methylethyl)phenyl and $R_2$ is 2,6-bis(1-methylethyl)phenyl or 2,4,6-tris-(1-methylelthyl)phenyl, wherein one of $R_1$ and $R_2$ is the group

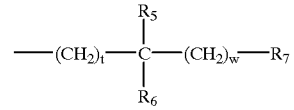

wherein t is zero or 1 to 4; w is zero or 1 to 4 with the proviso that the sum of t and w is not greater than 5; $R_5$ and $R_6$ are each independently selected from hydrogen or alkyl having from 1 to 6 carbon atoms, or when $R_5$ is hydrogen, $R_6$ can be selected from the groups defined for $R_7$; and $R_7$ is phenyl or phenyl substituted with from 1 to 3 substituents selected from a straight or branched alkyl group having from 1 to 6 carbon atoms, straight or branched alkoxy group having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —(CH$_2$)$_P$NR$_3$R$_4$ wherein P, R$_3$ and R$_4$ have the meanings defined above.

11. A method according to claim 1 wherein:

X is oxygen, sulfur or (CR'R")$_n$;

Y is oxygen, sulfur or (CR'R")$_n$ with the proviso that at least one of X or Y is (CR'R")$_n$ wherein n is an integer of from 1 to 4 and R' and R" are each independently hydrogen, straight or branched alkyl of from 1 to 6 carbons, optionally substituted phenyl, halogen, hydroxy, alkoxy, acyloxy, cycloalkyl, or R' and R" taken together form a carbonyl or a spirocycloalkyl group of from 3 to 10 carbons;

R is hydrogen;

R$_1$ is phenyl optionally substituted, straight or branched alkyl of from 1 to 10 carbon atoms, cycloalkyl of from 3 to 10 carbon atoms;

R$_2$ is phenyl optionally substituted, straight or branched alkyl of from 1 to 10 carbon atoms, cycloalkyl of from 3 to 8 carbon atoms, phenoxy optionally substituted with the proviso that only if X is (CR'R")$_n$ can R$_1$ be optionally substituted phenoxy and only if Y is (CR'R")$_n$ can R$_2$ be optionally substituted phenoxy, and with the further proviso that at least one of R$_1$ and R$_2$ is optionally substituted phenyl or phenoxy.

12. A method according to claim 1 wherein:

X is oxygen;

Y is (CR'R")$_n$ wherein n is an integer of from 1 to 2;

R is hydrogen;

R$_1$ is optionally substituted phenyl;

R$_2$ is optionally substituted phenyl or phenoxy, straight or branched alkyl of from 1 to 10 carbons, or cycloalkyl of from 3 to 10 carbons;

R' and R" are each independently hydrogen, straight or branched alkyl of from 1 to 6 carbons, optionally substituted phenyl, halogen, hydroxy, alkoxy, acyloxy, cycloalkyl, or R' and R" taken together form a carbonyl or a spirocycloalkyl.

13. A method according to claim 1 wherein the compound used is selected from:

Sulfamic acid (phenylacetyl)-2,6-bis(1-methylethyl) phenyl ester,

Sulfamic acid[[2,6-bis(1-methylethyl)phenyl]acetyl]-2,6-bis(1-methylethyl)phenyl ester, Sulfamic acid [[2,4,6-tris(1-methylethyl)phenyl]acetyl-2,4,6-tris(1-methylethyl)phenyl ester, Sulfamic acid[[2,6-bis(1-methylethyl)phenyl]acetyl]-2,4,6-tris(1-methylethyl)phenyl ester, Sulfamic acid[adamantaneacetyl]-2,6-bis[1-methylethyl) phenyl ester, Sulfamic acid[[2,6-bis(1-methylethyl)phenyl]acetyl]-2,6-bis(1-methylethyl)phenyl ester-sodium salt, Sulfamic acid[[2,4,6-tris(1-methylethyl)phenyl]acetyl]-2,6-bis(1-methylethyl)phenyl ester-sodium salt, Sulfamic acid (decanoyl)-2,6-bis-(1-methylethyl)phenyl ester, Sulfamic acid (dodecanoyl)-2,6-bis-(1-methylethyl) phenyl ester, 2,6-Bis(1-methylethyl)-N-[[[2,4,6-tris(1-methylethyl) phenyl]methyl]sulfonyl]benzeneacetamide, 2,6-Bis(1-methylethyl)-N-[[[2,4,6-tris(1-methylethyl) phenyl]methyl]sulfonyl]benzene-acetamide-sodium salt, 2,6-Bis(1-methylethyl)phenyl[[[2,4,6-tris(1-methylethyl) phenyl]methyl]sulfonyl)carbamate, 2,6-Bis(1-methylethyl)phenyl[[[2,4,6-tris(1-methylethyl) phenyl]methyl]sulfonyl]carbamate-sodium salt, Sulfamic acid (1-oxo-3,3-diphenylpropyl)-2,6-bis(1-methylethyl)phenyl ester, Sulfamic acid [2,6-dichlorophenyl(acetyl)]-2,6-bis(1-methylethyl)phenyl ester, Sulfamic acid [2,6-dichlorophenyl(acetyl)]-2,6-bis(1-methylethyl)phenyl ester, Sulfamic acid trans-[(2-phenylcyclopropyl)carbonyl]-2,6-bis(1-methylethyl)phenyl ester, Sulfamic acid [2,5-dimethoxyphenyl(acetyl)]-2,6-bis(1-methylethyl)phenyl ester, Sulfamic acid [2,4,6-trimethoxyphenyl(acetyl)]-2,6-bis(1-methylethyl)phenyl ester, Sulfamic acid [2,4,6-trimethylphenyl(acetyl)]-2,6-bis(1-methylethyl)phenyl ester, Sulfamic acid [2-thiophenyl(acetyl)]-2,6-bis(1-methylethyl)phenyl ester, Sulfamic acid [3-thiophenyl(acetyl)]-2,6-bis(1-methylethyl)phenyl ester, Sulfamic acid [2-methoxyphenyl(acetyl)]-2,6-bis(1-methylethyl)phenyl ester, Sulfamic acid (oxophenylacetyl)-2,6-bis(1-methylethyl) phenyl ester, Sulfamic acid [2-trifluoromethylphenyl(acetyl)]-2,6-bis(1-methylethyl)phenyl ester, Sulfamic acid (1-oxo-2-phenylpropyl)-2,6-bis(1-methylethyl)phenyl ester, Sulfamic acid (cyclopentylphenylacetyl)-2,6-bis(1-methylethyl)phenyl ester, Sulfamic acid (cyclohexylacetyl)-2,6-bis(1-methylethyl) phenyl ester, Sulfamic acid (diphenylacetyl)-2,6-bis(1-methylethyl) phenyl ester, Sulfamic acid (triphenylacetyl)-2,6-bis(1-methylethyl) phenyl ester, Sulfamic acid [(1-phenylcyclopentyl)carbonyl]-2,6-bis(1-methylethyl)phenyl ester, Sulfamic acid (3-methyl-1-oxo-2-phenylpentyl)-2,6-bis(1-methylethyl)phenyl ester, Sulfamic acid (1-oxo-2-phenylbutyl)-2,6-bis(1-methylethyl)phenyl ester, Sulfamic acid (cyclohexylphenylacetyl)-2,6-bis(1-methylethyl)phenyl ester, Sulfamic acid (1-oxo-2,2-diphenylpropyl)-2,6-bis(1-methylethyl)phenyl ester, Sulfamic acid [(9H-fluoren-9-yl)carbonyl]-2,6-bis(1-methylethyl)phenyl ester, Sulfamic acid (1-oxo-3-phenylpropyl)-2,6-bis(1-methylethyl)phenyl ester, Sulfamic acid [1-oxo-3-[2,4,6-tris(1-methylethyl) phenyl]-2-propenyl]-2,6-bis(1-methylethyl)phenyl ester, Sulfamic acid [1-oxo-3-[2,4,6-tris(1-methylethyl)phenyl] propyl]-2,6-bis(1-methylethyl)phenyl ester, Sulfamic acid [(acetyloxy)[2,4,6-tris(1-methylethyl)phenyl]acetyl]-2,6-bis(1-methylethyl)phenyl ester, Sulfamic acid [hydroxy[2,4,6-tris(1-methyl-ethyl)phenyl]acetyl]-2,6-bis(1-methylethyl)phenyl ester, Sulfamic acid [fluoro[2,4,6-tris(1-methylethyl)phenyl]acetyl]-2,6-bis(1-methylethyl)phenyl ester, Sulfamic acid (3-methyl-1-oxo-2-phenylpentyl)-2,6-bis(1-methylethyl)phenyl ester sodium salt, Sulfamic acid [[2,4,6-tris(1-methylethyl)phenoxy]acetyl]-2,6-bis(1-methylethyl)phenyl ester, Sulfamic acid [[2,6-bis(1-methylethyl)phenoxy]acetyl]-2,6-bis(1-methylethyl)phenyl ester, and Sulfamic acid [[2,4,6-tris(1-methylethyl)phenyl]acetyl]-2,6-bis(phenyl)phenyl ester.

14. A method according to claim 1 wherein sulfamic acid[[2,4,6-tris(1-methylethyl)phenyl]acetyl-2,6-bis(1-methylethyl)phenyl ester is administered.

15. A method of treating peripheral vascular disease comprising administering to a mammal in need of said treatment a therapeutically effective amount of a compound of formula:

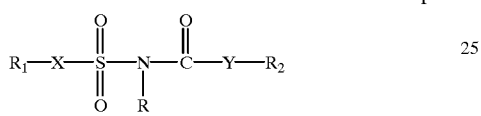

I or a pharmaceutically acceptable salt thereof wherein:
X and Y are selected from oxygen, sulfur and $(CR'R'')_n$ wherein n is an integer of from 1 to 4 and R' and R" are each independently hydrogen, alkyl, alkoxy, halogen, hydroxy, acyloxy, cycloalkyl, phenyl optionally substituted or R' and R" together form a spirocycloalkyl or a carbonyl; with the proviso at least one of X and Y is $(CR'R'')_n$ and with the further proviso when X and Y are both $(CR'R'')_n$ and R' and R" are hydrogen and n is one, $R_1$ and $R_2$ are aryl;

R is hydrogen, a straight or branched alkyl of from 1 to 8 carbon atoms or benzyl;

$R_1$ and $R_2$ are each independently selected from
(a) phenyl or phenoxy each of which is unsubstituted or is substituted with 1 to 5 substituents selected from phenyl,
an alkyl group having from 1 to 6 carbon atoms and which is straight or branched,
an alkoxy group having from 1 to 6 carbon atoms and which is straight or branched;
phenoxy,
hydroxy,
fluorine,
chlorine,
bromine,
nitro,
trifluoromethyl,
—COOH,
—COOalkyl wherein alkyl has from 1 to 4 carbon atoms and is straight or branched,
—$(CH_2)_pNR_3R_4$ wherein p is zero or one, and each of $R_3$ and $R_4$ is selected from hydrogen or a straight or branched alkyl group having 1 to 4 carbon atoms;
(b) 1- or 2-naphthyl unsubstituted or substituted with from 1 to 3 substituents selected from
phenyl,
an alkyl group having from 1 to 6 carbon atoms and which is straight or branched, an alkoxy group having from 1 to 6 carbon atoms and which is straight or branched;
hydroxy,
phenoxy,
fluorine,
chlorine,
bromine,
nitro,
trifluoromethyl,
—COOH,
—COOalkyl wherein alkyl has from 1 to 4 carbon atoms and is straight or branched,
—$(CH_2)_pNR_3R_4$ wherein p, $R_3$ and $R_4$ have the meanings defined above;
(c) arylalkyl;
(d) a straight or branched alkyl chain having from 1 to 20 carbon atoms and which is saturated or contains from 1 to 3 double bonds; or
(e) adamantyl or a cycloalkyl group wherein the cycloalkyl moiety has from 3 to 6 carbon atoms;
with the provisos.
(i) where X is $(CH_2)_n$, Y is oxygen, and $R_1$ is a substituted phenyl, then $R_2$ is a substituted phenyl;
(ii) where Y is oxygen, X is $(CH_2)_n$, $R_2$ is phenyl or naphthyl, then $R_1$ is not a straight or branched alkyl chain; and
(iii) the following compounds are excluded:

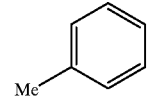

16. A method according to claim 15 wherein the compound administered is selected from:
Sulfamic acid (phenylacetyl)-2,6-bis(1-methylethyl)phenyl ester,
Sulfamic acid[[2,6-bis(1-methylethyl)phenyl]acetyl]-2,6-bis(1-methylethyl)phenyl ester,
Sulfamic acid [[2,4,6-tris(1-methylethyl)phenyl]acetyl-2,4,6-tris(1-methylethyl)phenyl ester,
Sulfamic acid[[2,6-bis(1-methylethyl)phenyl]acetyl]-2,4,6-tris(1-methylethyl)phenyl ester,
Sulfamic acid[adamantaneacetyl]-2,6-bis[1-methylethyl)phenyl ester,
Sulfamic acid[[2,6-bis(1-methylethyl)phenyl]acetyl]-2,6-bis(1-methylethyl)phenyl ester-sodium salt,
Sulfamic acid[[2,4,6-tris(1-methylethyl)phenyl]acetyl]-2,6-bis(1-methylethyl)phenyl ester-sodium salt,
Sulfamic acid (decanoyl)-2,6-bis-(1-methylethyl)phenyl ester,
Sulfamic acid (dodecanoyl)-2,6-bis-(1-methylethyl)phenyl ester,
2,6-Bis(1-methylethyl)-N-[[[2,4,6-tris(1-methylethyl)phenyl]methyl]sulfonyl]benzene-acetamide,
2,6-Bis(1-methylethyl)-N-[[[2,4,6-tris(1-methylethyl)phenyl]methyl]sulfonyl]benzene-acetamide-sodium salt,
2,6-Bis(1-methylethyl)phenyl[[[2,4,6-tris(1-methylethyl)phenyl]methyl]sulfonyl]carbamate, 2,6-Bis(1-methylethyl)phenyl[[[2,4,6-tris(1-methylethyl)
  phenyl]methyl]sulfonyl]carbamate-sodium salt,
Sulfamic acid (1-oxo-3,3-diphenylpropyl)-2,6-bis(1-
  methylethyl)phenyl ester,
Sulfamic acid [2,6-dichlorophenyl(acetyl)]-2,6-bis(1-
  methylethyl)phenyl ester,
Sulfamic acid [2,6-dichlorophenyl(acetyl)]-2,6-bis(1-
  methylethyl)phenyl ester,
Sulfamic acid trans-[(2-phenylcyclopropyl)carbonyl]-2,
  6-bis(1-methylethyl)phenyl ester,
Sulfamic acid [2,5-dimethoxyphenyl(acetyl)]-2,6-bis(1-
  methylethyl)phenyl ester,
Sulfamic acid [2,4,6-trimethoxyphenyl(acetyl)]-2,6-bis
  (1-methylethyl)phenyl ester,
Sulfamic acid [2,4,6-trimethylphenyl(acetyl)]-2,6-bis(1-
  methylethyl)phenyl ester,
Sulfamic acid (2-thiophenyl(acetyl)]-2,6-bis(1-
  methylethyl)phenyl ester,
Sulfamic acid (3-thiophenyl(acetyl)]-2,6-bis(1-
  methylethyl)phenyl ester,
Sulfamic acid [2-methoxyphenyl(acetyl)]-2,6-bis(1-
  methylethyl)phenyl ester,
Sulfamic acid (oxophenylacetyl)-2,6-bis(1-methylethyl)
  phenyl ester,
Sulfamic acid [2-trifluoromethylphenyl(acetyl)]-2,6-bis
  (1-methylethyl)phenyl ester,
Sulfamic acid (1-oxo-2-phenylpropyl)-2,6-bis(1-
  methylethyl)phenyl ester,
Sulfamic acid (cyclopentylphenylacetyl)-2,6-bis(1-
  methylethyl)phenyl ester,
Sulfamic acid (cyclohexylacetyl)-2,6-bis(1-methylethyl)
  phenyl ester,
Sulfamic acid (diphenylacetyl)-2,6-bis(1-methylethyl)
  phenyl ester,
Sulfamic acid (triphenylacetyl)-2,6-bis(1-methylethyl)
  phenyl ester,
Sulfamic acid ((1-phenylcyclopentyl)carbonyl]-2,6-bis(1-
  methylethyl)phenyl ester,
Sulfamic acid (3-methyl-1-oxo-2-phenylpentyl)-2,6-bis
  (1-methylethyl)phenyl ester,
Sulfamic acid (1-oxo-2-phenylbutyl)-2,6-bis(1-
  methylethyl)phenyl ester,
Sulfamic acid (cyclohexylphenylacetyl)-2,6-bis(1-
  methylethyl)phenyl ester,
Sulfamic acid (1-oxo-2,2-diphenylpropyl)-2,6-bis(1-
  methylethyl)phenyl ester,
Sulfamic acid [(9H-fluoren-9-yl)carbonyl]-2,6-bis(1-
  methylethyl)phenyl ester,
Sulfamic acid (1-oxo-3-phenylpropyl)-2,6-bis(1-
  methylethyl)phenyl ester,
Sulfamic acid [1-oxo-3-[2,4,6-tris(1-methylethyl)
  phenyl]-2-propenyl]-2,6-bis(1-methylethyl)phenyl
  ester,
Sulfamic acid [1-oxo-3-[2,4,6-tris(1-methylethyl)phenyl]
  propyl]-2,6-bis(1-methylethyl)phenyl ester,
Sulfamic acid [(acetyloxy)[2,4,6-tris(1-methylethyl)
  phenyl]acetyl]-2,6-bis(1-methylethyl)phenyl ester,
Sulfamic acid [hydroxy[2,4,6-tris(1-methylethyl)phenyl]
  acetyl]-2,6-bis(1-methylethyl)phenyl ester,
Sulfamic acid [fluoro[2,4,6-tris(1-methylethyl)phenyl]
  acetyl]-2,6-bis(1-methylethyl)phenyl ester,
Sulfamic acid (3-methyl-1-oxo-2-phenylpentyl)-2,6-bis
  (1-methylethyl)phenyl ester sodium salt, Sulfamic acid [[2,4,6-tris(1-methylethyl)phenoxy]
  acetyl]-2,6-bis(1-methylethyl)phenyl ester,
Sulfamic acid [[2,6-bis(1-methylethyl)phenoxy]acetyl3-
  2,6-bis(1-methylethyl)phenyl ester, and
Sulfamic acid [[2,4,6-tris(1-methylethyl)phenyl]acetyl]-
  2,6-bis(phenyl)phenyl ester.

17. A method of treating peripheral vascular disease comprising administering to a patient in need of said treatment a compound named sulfamic acid [[2,4,6-tris-(1-methylethyl)phenyl]acetyl-2,6-bis(1-methylethyl)phenyl ester.

18. A method of treating restenosis comprising:
    administering to a mammal in need of said treatment a therapeutically effective amount of a compound of formula:

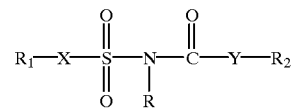

or a pharmaceutically acceptable salt thereof wherein:
  X and Y are selected from oxygen, sulfur and $(CR'R'')_n$ wherein n is an integer of from 1 to 4 and R' and R'' are each independently hydrogen, alkyl, alkoxy, halogen, hydroxy, acyloxy, cycloalkyl, phenyl optionally substituted or R' and R'' together form a spirocycloalkyl or a carbonyl; with the proviso at least one of X and Y is $(CR'R'')_n$ and with the further proviso when X and Y are both $(CR'R'')_n$ and R' and R'' are hydrogen and n is one, $R_1$ and $R_2$ are aryl;
  R is hydrogen, a straight or branched alkyl of from 1 to 8 carbon atoms or benzyl;
  $R_1$ and $R_2$ are each independently selected from
    (a) phenyl or phenoxy each of which is unsubstituted or is substituted with 1 to 5 substituents selected from
      phenyl,
      an alkyl group having from 1 to 6 carbon atoms and which is straight or branched,
      an alkoxy group having from 1 to 6 carbon atoms and which is straight or branched;
      phenoxy,
      hydroxy,
      fluorine,
      chlorine,
      bromine,
      nitro,
      trifluoromethyl,
      —COOH,
      —COOalkyl wherein alkyl has from 1 to 4 carbon atoms and is straight or branched,
      —$(CH_2)_p NR_3 R_4$ wherein p is zero or one, and each of $R_3$ and $R_4$ is selected from hydrogen or a straight or branched alkyl group having 1 to 4 carbon atoms;
    (b) 1- or 2-naphthyl unsubstituted or substituted with from 1 to 3 substituents selected from
      phenyl,
      an alkyl group having from 1 to 6 carbon atoms and which is straight or branched,
      an alkoxy group having from 1 to 6 carbon atoms and which is straight or branched;
      hydroxy,
      phenoxy,
      fluorine,
      chlorine, bromine,
nitro,
trifluoromethyl,
—COOH,
—COOalkyl wherein alkyl has from 1 to 4 carbon atoms and is straight or branched,
—(CH$_2$)$_p$NR$_3$R$_4$ wherein p, R$_3$ and R$_4$ have the meanings defined above;
(c) arylalkyl;
(d) a straight or branched alkyl chain having from 1 to 20 carbon atoms and which is saturated or contains from 1 to 3 double bonds; or
(e) adamantyl or a cycloalkyl group wherein the cycloalkyl moiety has from 3 to 6 carbon atoms;
with the provisos:
(i) where X is (CH$_2$)$_n$, Y is oxygen, and R$_1$ is a substituted phenyl, then R$_2$ is a substituted phenyl;
(ii) where Y is oxygen, X is (CH$_2$)$_n$, R$_2$ is phenyl or naphthyl, then R$_1$ is not a straight or branched alkyl chain; and
(iii) the following compounds are excluded:

| X | Y | R | R$_1$ | R$_2$ |
|---|---|---|---|---|
| CH$_2$ | O | H | (CH$_2$)$_2$CH$_3$ | Ph |
| CH$_2$ | O | H | CH$_3$ | Ph |
| CH$_2$ | O | H |  | i-Pr. |

(with a tolyl group shown for the last R$_2$)

19. A method of treating restenosis according to claim 18 wherein the compound administered is selected from:

Sulfamic acid (phenylacetyl)-2,6-bis(1-methylethyl)phenyl ester,
Sulfamic acid[[2,6-bis(1-methylethyl)phenyl]acetyl]-2,6-bis(1-methylethyl)phenyl ester,
Sulfamic acid [[2,4,6-tris(1-methylethyl)phenyl]acetyl-2,4,6-tris(1-methylethyl)phenyl ester,
Sulfamic acid[[2,6-bis(1-methylethyl)phenyl]acetyl]-2,4,6-tris(1-methylethyl)phenyl ester,
Sulfamic acid[adamantaneacetyl]-2,6-bis[1-methylethyl)phenyl ester,
Sulfamic acid[[2,6-bis(1-methylethyl)phenyl]acetyl]-2,6-bis(1-methylethyl)phenyl ester-sodium salt,
Sulfamic acid[[2,4,6-tris(1-methylethyl)phenyl]acetyl]-2,6-bis(1-methylethyl)phenyl ester-sodium salt,
Sulfamic acid (decanoyl)-2,6-bis-(1-methylethyl)phenyl ester,
Sulfamic acid (dodecanoyl)-2,6-bis-(1-methylethyl)phenyl ester,
2,6-Bis(1-methylethyl)-N-[[[2,4,6-tris(1-methylethyl)phenyl]methyl]sulfonyl]benzene-acetamide,
2,6-Bis(1-methylethyl)-N-[[[2,4,6-tris(1-methylethyl)phenyl]methyl]sulfonyl]benzene-acetamide-sodium salt,
2,6-Bis(1-methylethyl)phenyl[[[2,4,6-tris(1-methylethyl)phenyl]methyl]sulfonyl]carbamate,
2,6-Bis(1-methylethyl)phenyl[[[2,4,6-tris(1-methylethyl)phenyl]methyl]sulfonyl]carbamate-sodium salt,
Sulfamic acid (1-oxo-3,3-diphenylpropyl)-2,6-bis(1-methylethyl)phenyl ester,
Sulfamic acid [2,6-dichlorophenyl(acetyl)]-2,6-bis(1-methylethyl)phenyl ester,
Sulfamic acid [2,6-dichlorophenyl(acetyl)]-2,6-bis(1-methylethyl)phenyl ester,
Sulfamic acid trans-[(2-phenylcyclopropyl)carbonyl]-2,6-bis(1-methylethyl)phenyl ester,
Sulfamic acid [2,5-dimethoxyphenyl(acetyl)]-2,6-bis(1-methylethyl)phenyl ester,
Sulfamic acid [2,4,6-trimethoxyphenyl(acetyl)]-2,6-bis(1-methylethyl)phenyl ester,
Sulfamic acid [2,4,6-trimethylphenyl(acetyl)]-2,6-bis(1-methylethyl)phenyl ester,
Sulfamic acid [2-thiophenyl(acetyl)]-2,6-bis(1-methylethyl)phenyl ester,
Sulfamic acid [3-thiophenyl(acetyl)]-2,6-bis(1-methylethyl)phenyl ester,
Sulfamic acid [2-methoxyphenyl(acetyl)]-2,6-bis(1-methylethyl)phenyl ester,
Sulfamic acid (oxophenylacetyl)2,6-bis(1-methylethyl)phenyl ester,
Sulfamic acid [2-trifluoromethylphenyl(acetyl)]-2,6-bis(1-methylethyl)phenyl ester,
Sulfamic acid (1-oxo-2-phenylpropyl)-2,6-bis(1-methylethyl)phenyl ester,
Sulfamic acid (cyclopentylphenylacetyl)-2,6-bis(1-methylethyl)phenyl ester,
Sulfamic acid (cyclohexylacetyl)-2,6-bis(1-methylethyl)phenyl ester,
Sulfamic acid (diphenylacetyl)-2,6-bis(1-methylethyl)phenyl ester,
Sulfamic acid (triphenylacetyl)-2,6-bis(1-methylethyl)phenyl ester,
Sulfamic acid [(1-phenylcyclopentyl)carbonyl]-2,6-bis(1-methylethyl)phenyl ester,
Sulfamic acid (3-methyl-1-oxo-2-phenylpentyl)-2,6-bis(1-methylethyl)phenyl ester,
Sulfamic acid (1-oxo-2-phenylbutyl)-2,6-bis(1-methylethyl)phenyl ester,
Sulfamic acid (cyclohexylphenylacetyl)-2,6-bis(1-methylethyl)phenyl ester,
Sulfamic acid (1-oxo-2,2-diphenylpropyl)-2,6-bis(1-methylethyl)phenyl ester,
Sulfamic acid [(9H-fluoren-9-yl)carbonyl]-2,6-bis(1-methylethyl)phenyl ester,
Sulfamic acid (1-oxo-3-phenylpropyl)-2,6-bis(1-methylethyl)phenyl ester,
Sulfamic acid [1-oxo-3-[2,4,6-tris(1-methylethyl)phenyl]-2-propenyl]-2,6-bis-(1-methylethyl)phenyl ester,
Sulfamic acid [1-oxo-3-[2,4,6-tris(1-methylethyl)phenyl]propyl]-2,6-bis(1-methylethyl)phenyl ester,
Sulfamic acid [(acetyloxy)[2,4,6-tris(1-methylethyl)phenyl]acetyl]-2,6-bis(1-methylethyl)phenyl ester,
Sulfamic acid [hydroxy[2,4,6-tris(1-methylethyl)phenyl]acetyl]-2,6-bis(1-methylethyl)phenyl ester,
Sulfamic acid [fluoro[2,4,6-tris(1-methylethyl)phenyl]acetyl]-2,6-bis(1-methylethyl)phenyl ester,
Sulfamic acid (3-methyl-1-oxo-2-phenylpentyl)-2,6-bis(1-methylethyl)phenyl ester sodium salt,
Sulfamic acid [[2,4,6-tris(1-methylethyl)phenoxy]acetyl]-2,6-bis(1-methylethyl)phenyl ester,
Sulfamic acid [[2,6-bis(1-methylethyl)phenoxy]acetyl]-2,6-bis(1-methylethyl)phenyl ester, and Sulfamic acid [[2,4,6-tris(1-methylethyl)phenyl]acetyl]-2,6-bis(phenyl)phenyl ester.

20. A method of treating restenosis comprising administering to a patient in need of said treatment a compound named sulfamic acid [[2,4,6-tris-(1-methylethyl)phenyl]acetyl-2,6-bis(1-methylethyl)phenyl ester.

21. A method of treating cerebrovascular disease comprising administering to a mammal in need of said treatment a therapeutically effective amount of a compound of formula:

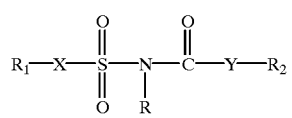

I or a pharmaceutically acceptable salt thereof wherein:

X and Y are selected from oxygen, sulfur and $(CR'R'')_n$ wherein n is an integer of from 1 to 4 and R' and R'' are each independently hydrogen, alkyl, alkoxy, halogen, hydroxy, acyloxy, cycloalkyl, phenyl optionally substituted or R' and R'' together form a spirocycloalkyl or a carbonyl; with the proviso at least one of X and Y is $(CR'R'')_n$ and with the further proviso when X and Y are both $(CR'R'')_n$ and R' and R'' are hydrogen and n is one, $R_1$ and $R_2$ are aryl;

R is hydrogen, a straight or branched alkyl of from 1 to 8 carbon atoms or benzyl;

$R_1$ and $R_2$ are each independently selected from
  (a) phenyl or phenoxy each of which is unsubstituted or is substituted with 1 to 5 substituents selected from
    phenyl,
    an alkyl group having from 1 to 6 carbon atoms and which is straight or branched,
    an alkoxy group having from 1 to 6 carbon atoms and which is straight or branched;
    phenoxy,
    hydroxy,
    fluorine,
    chlorine,
    bromine,
    nitro,
    trifluoromethyl,
    —COOH,
    —COOalkyl wherein alkyl has from 1 to 4 carbon atoms and is straight or branched,
    —$(CH_2)_pNR_3R_4$ wherein p is zero or one, and each of $R_3$ and $R_4$ is selected from hydrogen or a straight or branched alkyl group having 1 to 4 carbon atoms;
  (b) 1- or 2-naphthyl unsubstituted or substituted with from 1 to 3 substituents selected from
    phenyl,
    an alkyl group having from 1 to 6 carbon atoms and which is straight or branched,
    an alkoxy group having from 1 to 6 carbon atoms and which is straight or branched;
    hydroxy,
    phenoxy,
    fluorine,
    chlorine,
    bromine,
    nitro,
    trifluoromethyl,
    —COOH,
    —COOalkyl wherein alkyl has from 1 to 4 carbon atoms and is straight or branched,
    —$(CH_2)_pNR_3R_4$ wherein p, $R_3$ and $R_4$ have the meanings defined above;
  (c) arylalkyl;
  (d) a straight or branched alkyl chain having from 1 to 20 carbon atoms and which is saturated or contains from 1 to 3 double bonds; or
  (e) adamantyl or a cycloalkyl group wherein the cycloalkyl moiety has from 3 to 6 carbon atoms;
with the provisos:
  (i) where X is $(CH_2)_n$, Y is oxygen, and $R_1$ is a substituted phenyl, then $R_2$ is a substituted phenyl;
  (ii) where Y is oxygen, X is $(CH_2)_n$, $R_2$ is phenyl or naphthyl, then $R_1$ is not a straight or branched alkyl chain; and
  (iii) the following compounds are excluded:

| X | Y | R | $R_1$ | $R_2$ |
|---|---|---|---|---|
| $CH_2$ | O | H | $(CH_2)_2CH_3$ | Ph |
| $CH_2$ | O | H | $CH_3$ | Ph |
| $CH_2$ | O | H | 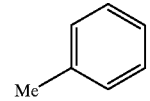 | i-Pr. |

22. A method of treating cerebrovascular disease according to claim 21 wherein the compound administered is selected from:

Sulfamic acid (phenylacetyl)-2,6-bis(1-methylethyl) phenyl ester,

Sulfamic acid[[2,6-bis(1-methylethyl)phenyl]acetyl]-2,6-bis(1-methylethyl)phenyl ester, Sulfamic acid [[2,4,6-tris(1-methylethyl)phenyl]acetyl-2,4,6-tris(1-methylethyl)phenyl ester, Sulfamic acid[[2,6-bis(1-methylethyl)phenyl]acetyl]-2,4,6-tris(1-methylethyl)phenyl ester, Sulfamic acid[adamantaneacetyl]-2,6-bis[1-methylethyl) phenyl ester, Sulfamic acid[[2,6-bis(1-methylethyl)phenyl]acetyl]-2,6-bis(1-methylethyl)phenyl ester-sodium salt, Sulfamic acid[[2,4,6-tris(1-methylethyl)phenyl]acetyl]-2,6-bis(1-methylethyl)phenyl ester-sodium salt, Sulfamic acid (decanoyl)-2,6-bis-(1-methylethyl)phenyl ester, Sulfamic acid (dodecanoyl)-2,6-bis-(1-methylethyl) phenyl ester, 2,6-Bis(1-methylethyl)-N-[[[2,4,6-tris(1-methylethyl) phenyl]methyl]sulfonyl]benzene-acetamide, 2,6-Bis(1-methylethyl)-N-[[[2,4,6-tris(1-methylethyl) phenyl]methyl]sulfonyl]benzene-acetamide-sodium salt, 2,6-Bis(1-methylethyl)phenyl[[[2,4,6-tris(1-methylethyl) phenyl]methyl]sulfonyl]carbamate, 2,6-Bis(1-methylethyl)phenyl[[[2,4,6-tris(1-methylethyl) phenyl]methyl]sulfonyl]carbamate-sodium salt, Sulfamic acid (1-oxo-3,3-diphenylpropyl)-2,6-bis(1-methylethyl)phenyl ester, Sulfamic acid [2,6-dichlorophenyl(acetyl)]-2,6-bis(1-methylethyl)phenyl ester, Sulfamic acid [2,6-dichlorophenyl(acetyl)]-2,6-bis(1-methylethyl)phenyl ester, Sulfamic acid trans-[(2-phenylcyclopropyl)carbonyl]-2,6-bis(1-methylethyl)phenyl ester, Sulfamic acid [2,5-dimethoxyphenyl(acetyl)]-2,6-bis(1-methylethyl)phenyl ester, Sulfamic acid [2,4,6-trimethoxyphenyl(acetyl)]-2,6-bis(1-methylethyl)phenyl ester, Sulfamic acid [2,4,6-trimethylphenyl(acetyl)]-2,6-bis(1-methylethyl)phenyl ester, Sulfamic acid [2-thiophenyl(acetyl)]-2,6-bis(1-methylethyl)phenyl ester, Sulfamic acid [3-thiophenyl(acetyl)]-2,6-bis(1-methylethyl)phenyl ester, Sulfamic acid [2-methoxyphenyl(acetyl)]-2,6-bis(1-methylethyl)phenyl ester, Sulfamic acid (oxophenylacetyl)-2,6-bis(1-methylethyl)phenyl ester, Sulfamic acid [2-trifluoromethylphenyl(acetyl)]-2,6-bis(1-methylethyl)phenyl ester, Sulfamic acid (1-oxo-2-phenylpropyl)-2,6-bis(1-methylethyl)phenyl ester, Sulfamic acid (cyclopentylphenylacetyl)-2,6-bis(1-methylethyl)phenyl ester, Sulfamic acid (cyclohexylacetyl)-2,6-bis(1-methylethyl)phenyl ester, Sulfamic acid (diphenylacetyl)-2,6-bis(1-methylethyl)phenyl ester, Sulfamic acid (triphenylacetyl)-2,6-bis(1-methylethyl)phenyl ester, Sulfamic acid [(1-phenylcyclopentyl)carbonyl]-2,6-bis(1-methylethyl)phenyl ester, Sulfamic acid (3-methyl-1-oxo-2-phenylpentyl)-2,6-bis(1-methylethyl)phenyl ester, Sulfamic acid (1-oxo-2-phenylbutyl)-2,6-bis(1-methylethyl)phenyl ester, Sulfamic acid (cyclohexylphenylacetyl)-2,6-bis(1-methylethyl)phenyl ester, Sulfamic acid (1-oxo-2,2-diphenylpropyl)-2,6-bis(1-methylethyl)phenyl ester, Sulfamic acid [(9H-fluoren-9-yl)carbonyl]-2,6-bis(1-methylethyl)phenyl ester, Sulfamic acid (1-oxo-3-phenylpropyl)-2,6-bis(1-methylethyl)phenyl ester, Sulfamic acid [1-oxo-3-[2,4,6-tris(1-methylethyl)phenyl]-2-propenyl]-2,6-bis(1-methylethyl)phenyl ester, Sulfamic acid [1-oxo-3-[2,4,6-tris(1-methylethyl)phenyl]propyl]-2,6-bis(1-methylethyl)phenyl ester, Sulfamic acid [(acetyloxy)r2,4,6-tris(1-methylethyl)phenyl]acetyl]-2,6-bis(1-methylethyl)phenyl ester, Sulfamic acid [hydroxy[2,4,6-tris(1-methylethyl)phenyl]acetyl]-2,6-bis(1-methylethyl)phenyl ester, Sulfamic acid [fluoro[2,4,6-tris(1-methylethyl)phenyl]acetyl]-2,6-bis(1-methylethyl)phenyl ester, Sulfamic acid (3-methyl-1-oxo-2-phenylpentyl)-2,6-bis(1-methylethyl)phenyl ester sodium salt, Sulfamic acid [[2,4,6-tris(1-methylethyl)phenoxy]acetyl]-2,6-bis(1-methylethyl)phenyl ester, Sulfamic acid [[2,6-bis(1-methylethyl)phenoxy]acetyl]-2,6-bis(1-methylethyl)phenyl ester, and Sulfamic acid [[2,4,6-tris(1-methylethyl)phenyl]acetyl]-2,6-bis(phenyl)phenyl ester.

23. A method of treating cerebrovascular disease comprising administering to a patient in need of said treatment a compound named sulfamic acid [[2,4,6-tris-(1-methylethyl)phenyl]acetyl-2,6-bis(1-methylethyl)phenyl ester.

* * * * *